(12) United States Patent
Sung et al.

(10) Patent No.: US 7,049,097 B2
(45) Date of Patent: May 23, 2006

(54) ANTIBIOTICS-INDEPENDENT VECTOR FOR CONSTANT HIGH-EXPRESSION AND METHOD FOR GENE EXPRESSION USING THE SAME

(75) Inventors: Moon Hee Sung, Daejeon (KR); Seung Goo Lee, Daejeon (KR); Seung Pyo Hong, Daejeon (KR); Eun Ja Yoon, Gyeongsangbuk-do (KR); Yoon Ho Choi, Suwon-si (KR); Ha Ryoung Poo, Daejeon (KR)

(73) Assignees: Bioleaders Corporation, Daejeon (KR); Korea Research Institute of Bioscience and Biotechnology, Daejeon (KR)

( * ) Notice: Subject to any disclaimer, the term of this patent is extended or adjusted under 35 U.S.C. 154(b) by 502 days.

(21) Appl. No.: 10/221,349

(22) PCT Filed: Jan. 11, 2002

(86) PCT No.: PCT/KR02/00048

§ 371 (c)(1),
(2), (4) Date: Sep. 11, 2002

(87) PCT Pub. No.: WO02/055716

PCT Pub. Date: Jul. 18, 2002

(65) Prior Publication Data

US 2003/0084474 A1    May 1, 2003

(30) Foreign Application Priority Data

Jan. 12, 2001   (KR)   .................... 10-2001-0001690

(51) Int. Cl.
*C12P 21/00*   (2006.01)
*C12N 15/61*   (2006.01)
*C12N 15/63*   (2006.01)
*C12N 9/90*    (2006.01)
*C12N 1/21*    (2006.01)

(52) U.S. Cl. ................. 435/69.1; 536/23.7; 435/320.1; 435/233; 435/252.33

(58) Field of Classification Search ............... 435/69.1, 435/320.1, 252.31, 252.33, 233; 536/23.2
See application file for complete search history.

(56) References Cited

U.S. PATENT DOCUMENTS 5,919,663 A    7/1999   Brey et al. .................. 435/69.3

FOREIGN PATENT DOCUMENTS

KR    0231919    1/1999

OTHER PUBLICATIONS

Ferrari E, Henner DJ, Yang MY, Isolation fo an alanine racemase gene rom *Bacilus subtilis* and its use for plasmid maintenance in *B. subtilis*, 1985, Bio/Technology 3:1003-1007.*

Galkin A, Kulakova L, Kurihara T, Yoshimura T, Esaki N, Proteins from cold-adapted bacteria: evolutionary and structural relationships with mesophilic and thermophilic counterparts, May 2000, Genbank Accession No. AF263927.*

Petty KJ, Metal-chelate affinity chromatography, in Current Protocols in Molecular Biology, Wiley and Sons, 1996, pp 10.11.10-10.11.24.*

* cited by examiner

*Primary Examiner*—Ram R. Shukla
*Assistant Examiner*—Patrick S. Riggins
(74) *Attorney, Agent, or Firm*—Staas & Halsey LLP (57) ABSTRACT

An antibiotic-independent vector for stable vector maintenance and high protein expression and a method for gene expression using this vector are disclosed. The stable maintenance of the vector is due to expression of a glutamic acid racemase to complement a D-glutamic acid auxotroph. No antibiotics, such as ampicillin, are necessary for the stable maintenance of this vector.

7 Claims, 6 Drawing Sheets

SEQUENCE LISTING

<160> NUMBER OF SEQ ID NOS: 2

<210> SEQ ID NO 1
<211> LENGTH: 910
<212> TYPE: DNA
<213> ORGANISM: Brevibacillus borstelensis

<400> SEQUENCE: 1

```
agcgaaaata aaaggaagtg gtatgctatt aggtatggac aacacaacag gggagacaca      60
ccgatgagcg accatgaatc cattgcaatc attgattccg gagtgggggg gctgactgtt     120
gccaaagaag tcatgcggca gttgcccggt gaatccattc tctatttcgg cgataatgcc     180
cgctgtcctt atgggtccag gacgccgaaa gaaatacgtg cctacagttt tcagatgatt     240
gagtttgtct cgaagtttcc gatcaaggcg ctcgtcattg cctgcaacac agcgacagcg     300
gtggtgctgg aagaagcgag gagaaggctt ccgttgccgg tcattggggt aatcgagccg     360
ggggcaaggg cagcgatcag cgtaacgaaa acagaccgga ttggggtgat cggaacagaa     420
accacgatcc gcaccaaagc atatgagcag gctgtcaagc gattgagacc cgattcatgt     480
gtagtcggac ttgcttgtcc tgccttcgtg cctctggtgg agacgcattg tcagcattca     540
gaggaagcgc aaaaagaggt ggagcggacc cttgagccgt gcagggtct cgaactggac      600
accttgattc tcgggtgcac gcactatccg ctgcttgcgc cattgattca gaaagccgtc     660
ggatcggggg ttgccctcat cagctcggcg gaggaaacgg cacgcgaggt aagccggttg     720
ctgggagacg tcacgaacgg tttggcgcgg ggaaaagagc gacctgcaga tcctcccaga     780
cactgctttt acacgagcgg aaatgcgctt tccttccagc gaatagcgga agaatggctg     840
ggctttccgg tacaggttga aagcaggtcg ctggaaaagc tgtatcaatc ctgagtcggc     900
aaataaacgc                                                            910
```

<210> SEQ ID NO 2
<211> LENGTH: 4665
<212> TYPE: DNA
<213> ORGANISM: Bacillus sp.

<400> SEQUENCE: 2

```
gatctctcct tcacagattc ccaatctctt gttaaataac gaaaaagcat caatcaaaac      60
ggcggcatgt cttttctatat tccagcaatg ttttataggg gacatattga tgaagatggg     120
tatcaccttta gtaaaaaaag aattgctata agctgctctt ttttgttcgt gatatactga     180
taataaattg aatttttcaca cttctggaaa aaggagatat accatggaat tcgagctcgg     240
tacccgggga tcctctagag tcgacctgca ggcatgcaag cttggctgtt ttggcggatg     300
agagaagatt ttcagcctga tacagattaa atcagaacgc agaagcggtc tgataaaaca     360
gaatttgcct ggcggcagta gcgcggtggt cccacctgac cccatgccga actcagaagt     420
gaaacgccgt agcgccgatg gtagtgtggg gtctccccat gcgagagtag ggaactgcca     480
ggcatcaaat aaaacgaaag gctcagtcga agactgggc cttttcgtttt atctgttgtt     540
tgtcggtgaa cgctctcctg agtaggacaa atccgccggg agcggatttg aacgttgcga     600
agcaacggcc cggagggtgg cgggcaggac gcccgccata aactgccagg catcaaatta     660
agcagaaggc catcctgacg gatggccttt tgcgttttct acaaactctt tttgtttatt     720
tttctaaata cattcaaata tgtatccgct catgagacaa taaccctgat aaatgcttca     780
ataatattga aaaggaaga gtatgagtat tcaacatttc cgtgtcgccc ttattcccctt     840
ttttgcggca ttttgccttc ctgttttttgc tcacccagaa acgctggtga agtaaaaga      900
tgctgaagat cagttgggtg cacgagtggg ttacatcgaa ctggatctca acagcggtaa     960
gatccttgag agttttcgcc ccgaagaacg ttttccaatg atgagcactt ttaaagttct    1020
gctatgtggc gcggtattat cccgtgttga cgccgggcaa gagcaactcg gtcgccgcat    1080
acactattct cagaatgact tggttgagta attcactggc cgtcgtttta caacgtcgtg    1140
```

-continued

```
actgggaaaa ccctggcgtt acccaactta atcgccttgc agcacatccc cctttcgcca    1200
gctggcgtaa tagcgaagag gcccgcaccg atcgcccttc ccaacagttg cgcagcctga    1260
atggcgaatg gcgcctgatg cggtattttc tccttacgca tctgtgcggt atttcacacc    1320
gcatagcgtt tatttgccga ctcaggattg atacagcttt ccagcgacc tgctttcaac     1380 ctgtaccgga aagcccagcc attcttccgc tattcgctgg aaggaaagcg catttccgct    1440
cgtgtaaaag cagtgtctgg gaggatctgc aggtcgctct ttccccgcg ccaaaccgtt     1500 cgtgacgtct cccagcaacc ggcttacctc gcgtgccgtt cctccgccg agctgatgag     1560 ggcaaccccc gatccgacgg ctttctgaat caatggcgca agcagcggat agtgcgtgca    1620
cccgagaatc aaggtgtcca gttcgagacc ctgcaacggc tcaagggtcc gctccacctc    1680
tttttgcgct tcctctgaat gctgacaatg cgtctccacc agaggcacga aggcaggaca    1740
agcaagtccg actacacatg aatcgggtct caatcgcttg acagcctgct catatgcttt    1800
ggtgcggatc gtggtttctg ttccgatcac cccaatccgg tctgttttcg ttacgctgat    1860
cgctgccctt gccccggct cgattacccc aatgaccggc aacggaagcc ttctcctcgc     1920
ttcttccagc accaccgctg tcgctgtgtt gcaggcaatg acgagcgcct tgatcggaaa    1980
cttcgagaca aactcaatca tctgaaaact gtaggcacgt atttcttccg gcgtcctgga    2040
cccataagga cagcgggcat tatcgccgaa atagagaatg gattcaccgg gcaactgccg    2100
catgacttct ttggcaacag tcagccccc cactccggaa tcaatgattg caatggattc      2160
atggtcgctc atcggtgtgt ctcccctgtt gtgttgtcca tacctaatag cataccactt    2220
ccttttattt tcgcttatgg tgcactctca gtacaatctg ctctgatgcc gcatagttaa    2280
gccagccccg acaccgcca acaccgctg acgcgcctg acgggcttgt ctgctcccgg        2340
catccgctta cagacaagct gtgaccgtct ccgggagctg catgtgtcag aggttttcac    2400
cgtcatcacc gaaacgcgcg agacgaaagg gcctcgtgat acgcctattt ttataggtta    2460
atgtcatgat aataatggtt tcttagacgt caggtggcac ttttcgggga aatgtgcgcg    2520
gaacccctat ttgtttattt ttctaaatac attcaaatat gtatccgctc atgagacaat    2580
aaccctgata aatgcttcaa taatattgaa aaggaagag tatgagtatt caacatttcc     2640
gtgtcgccct tattccctt tttgcggcat tttgccttcc tgttttgct cacccagaaa      2700 cgctggtgaa agtaaaagat gctgaagatc agttgggtgc acgagtgggt tacatcgaac    2760
tggatctcaa cagcggtaag atccttgaga gttttcgccc cgaagaacgt tttccaatga    2820
tgagcacttt taaagttctg ctatgtggcg cggtattatc ccgtattgac gccgggcaag    2880
agcaactcgg tcgccgcata cactattctc agaatgactt ggttgagtac tcaccagtca    2940
cagaaaagca tcttacggat ggcatgacag taagagaatt atgcagtgct gccataacca    3000
tgagtgataa cactgcggcc aacttacttc tgacaacgat cggaggaccg aaggagctaa    3060 ccgcttttt gcacaacatg gggatcatg taactcgcct tgatcgttgg gaaccggagc      3120
tgaatgaagc cataccaaac gacgagcgtg acaccacgat gcctgtagca atggcaacaa    3180
cgttgcgcaa actattaact ggcgaactac ttactctagc ttcccggcaa caattaatag    3240
actggatgga ggcggataaa gttgcaggac cacttctgcg ctcggccctt ccggctggct    3300
ggtttattgc tgataaatct ggagccggtg agcgtgggtc tcgcggtatc attgcagcac    3360
tggggccaga tggtaagccc tcccgtatcg tagttatcta cacgacgggg agtcaggcaa    3420
ctatggatga acgaaataga cagatcgctg agataggtgc ctcactgatt aagcattggt    3480
```

-continued

```
aactgtcaga ccaagtttac tcatatatac tttagattga tttaaaactt cattttaat    3540
ttaaaaggat ctaggtgaag atcctttttg ataatctcat gaccaaaatc ccttaacgtg    3600
agttttcgtt ccactgagcg tcagaccccg tagaaaagat caaaggatct tcttgagatc    3660
cttttttcct gcgcgtaatc tgctgcttgc aaacaaaaaa accaccgcta ccagcggtgg    3720
tttgtttgcc ggatcaagag ctaccaactc ttttccgaa ggtaactggc ttcagcagag    3780
cgcagatacc aaatactgtc cttctagtgt agccgtagtt aggccaccac ttcaagaact    3840
ctgtagcacc gcctacatac ctcgctctgc taatcctgtt accagtggct gctgccagtg    3900
gcgataagtc gtgtcttacc gggttggact caagacgata gttaccggat aaggcgcagc    3960
ggtcgggctg aacggggggt tcgtgcacac agcccagctt ggagcgaacg acctacaccg    4020
aactgagata cctacagcgt gagcattgag aaagcgccac gcttcccgaa gggagaaagg    4080
cggacaggta tccggtaagc ggcagggtcg gaacaggaga gcgcacgagg gagcttccag    4140
ggggaaacgc ctggtatctt tatagtcctg tcgggtttcg ccacctctga cttgagcgtc    4200
gatttttgtg atgctcgtca ggggggcgga gcctatggaa aaacgccagc aacgcggcct    4260
ttttacggtt cctggccttt tgctggcctt ttgctcacat gttctttcct gcgttatccc    4320
ctgattctgt ggataaccgt attaccgcct ttgagtgagc tgataccgct cgccgcagcc    4380
gaacgaccga gcgcagcgag tcagtgagcg aggaagcgga agagcgccca atacgcaaac    4440
cgcctctccc cgcgcgttgg ccgattcatt aatgcagctg gcacgacagg tttcccgact    4500
ggaaagcggg cagtgagcgc aacgcaatta atgtgagtta gctcactcat taggcaccc    4560
aggctttaca ctttatgctt ccggctcgta tgttgtgtgg aattgtgagc ggataacaat    4620
ttcacacagg aaacagctat gaccatgatt acgccaagct agctt                   4665
```

ANTIBIOTICS-INDEPENDENT VECTOR FOR CONSTANT HIGH-EXPRESSION AND METHOD FOR GENE EXPRESSION USING THE SAME

This application is the National Stage of International Application No. PCT/KR02/00048, filed Jan. 11, 2002, published as WO 02/055,716 on Jul. 18, 2002.

BACKGROUND OF THE INVENTION

1. Technical Field

The present invention relates to an antibiotic-independent vector for constant high-expression. More particularly, the invention relates to a high-expression vector in which a recombinant gene can be stably transcribed and highly expressed, since antibiotic-resistant genes, such as ampicillin and the like, are not utilized, while genes essential for cell growth and proliferation are adopted as a selective marker to secure a stable gene expression system.

2. Background Art

To manufacture useful proteins using a genetic engineering technique, an expression system is used that exploits a proper promoter and host cell established in its culture protocol. Precisely, microbes, such as *Escherichia coli*, *Bacillus subtilis*, and *Saccharomyces cerevisiae* etc., animal cells, insect cells, and plant cells can all be selected as host cells. In addition, to replicate plasmids consistently, an antibiotic-resistant gene is inserted into the cloning vector, which is then fermented based on the addition of antibiotics into the culture medium or a proper inducer for the high-expression of the target gene.

Generally, ampicillin, kanamycin, tetracycline, or the like are adopted as a selective marker during the fermentation to perform the gene cloning and produce recombinant enzymes for industrial uses and recombinant proteins for medical purposes. However, such antibiotic-resistant genes are apt to lose their activity over time. Therefore, in a continuous fermentation process, the cultured product of the host cells is degraded or diluted as the number of generations increases. The antibiotics added into the culture medium decompose, the stability of the highly sensitive plasmids decreases, and thus the amount of proteins expressed from the cloned exogenous genes also decreases. In the case that the protein is a kind of food additive, the antibiotics added for the cultivation must be removed before proceeding to the expression. This also results in high costs for gene production on a large scale, as inducers such as isopropyl-β-D-thiogalactoside(IPTG) are expensive.

Accordingly, many studies have already attempted to overcome the foregoing and other disadvantages. Concretely, Korean Patent Registration No. 0231919 discloses an expression vector that exploits the temperature induction of a phage λ promoter instead of the expensive IPTG and includes the application of an antibiotic-resistant gene. However, when induction methods are used that involve temperature without inducers, temperature increases are hard to manage optimally. Also, the expression ratio is lower than that in conventional methods using inducers. U.S. Pat. No. 5,919,663 illustrates that the modified pur A vector (adenylosuccinate synthetase) can be applied to maintain a stable plasmid without the use of an antibiotic-resistant gene. Presently, auxotrophic strains are used to minimize the production of amino acids and by-products inhibiting the synthesis of target amino acids. However, if mutant strains are deficient as synthetic genes in the amino acids essential for cell growth, a refined medium rather than a complex one is required in which the L-amino acid content has been adjusted, namely the composition of the medium is quantified.

Therefore, a novel gene expression system is required that facilitates stable gene production, reduces costs, and provides excellent industrial application.

SUMMARY OF THE INVENTION

An objective of the present invention is to provide a novel high-expression vector in which a recombinant gene can be stably transcribed and highly expressed without the use of antibiotic-resistant genes, such as ampicillin and the like, based on the adoption of genes essential for cell growth and proliferation as a selective marker to secure stability, and to produce transformed cells in which said high-expression vector is introduced.

Another objective of the present invention is to provide a promoter that can provide high-level expression of a target gene, even without induction, recombinant DNA containing intracellular essential genes, gene expression vectors using said promoter, and a DNA and novel-gene expression system that exploits said transformed cells introduced by said high-expression vector.

The inventors of the present invention attempted to maintain the stability of the plasmids using a gene encoding glutamic acid racemase as a selective marker instead of an antibiotic-resistant gene. Glutamic acid racemase is an essential enzyme for the growth of microbes and participates in the synthesis of the cell wall. Peptidoglycan, required to sustain the physical force of the cell wall and intrinsic morphology of the cell, is composed of D-glutamic acid and D-alanine, yet their production is restricted in the biosynthetic pathway. As such, glutamic acid racemase is exploited for the biosynthesis of this essential D-glutamic acid. In the present invention, a mutant strain auxotropic to D-glutamic acid is used as the host, then its complementary gene is cloned and re-inserted into the novel expression vector. At this point, a constitutively and highly expressed promoter, separated from the conventional high-expression vector, pHCE19T(II), purchased from the Bioleaders Corporation, is exploited and the cloned gene is inserted so as to prepare the high-expression vector. The novel expression vector pHCE(III) is confirmed to have a 4665 bp size and maintain stability in case that the expression vector pHCE(III)-TPL is transferred to the host cell and cultivated through nine generations. Furthermore, it is also examined whether or not exogenous proteins can be produced to maintain stability on a large scale. Consequently, when the *Eschericlia coli* WM335 was transformed with expression vector pHCE(III)-TNA and cultivated, the production volume was found to increase about 9.2-fold compared with that obtained when using the IPTG promoter.

Hereinafter, the present invention will be explained more fully.

In the present invention, the gene encoding glutamic acid racemase (GluRa), which is essential for the survival of microbes, related to the composition of the cell wall, and derived from *Brevibacillus borstelensis*, is utilized as the selective marker. At this point, any essential gene participating in the composition of the cell wall can be adopted if it can synthesize amino acids, such as D-glutamic acid, D-alanine, and so on, including the gene encoding glutamic acid racemase. A D-glutamic acid-dependent mutant strain, mutated using the biosynthetic pathway of D-glutamic acid and *Escherichia coli* WM 335 strain is used as the preferable host cell.

Concretely, the chromosomal DNA of the *Bacillus* sp. strain is cleaved with restriction enzymes, then the DNA fragments are re-cloned into a plasmid vector, such as pUC19, to transform the mutant strain auxotropic to D-glutamic acid, WM 335 (J. Bacteriol., May, 1993, 2970–2979). Then, those colonies growing on a culture medium without D-glutamic acid are collected and the DNA encoding glutamic acid racemase is obtained.

In addition, DNA that has a complementary sequence and can hybridize under specific conditions and a gene prepared using oligonucleotide probes or primers designed on the basis of the above DNA through general procedures and chemical synthesis can also produce D-glutamic acid.

The nucleotide sequences of the oligonucleotide probes described above are not restricted. Any DNA that contains the above DNA or its complementary sequences is feasible if it can hybridize under stringent conditions. Hereinafter, the term "stringent conditions means" the following experimental conditions. The probe is reacted at Tm-20 through 30° C. in a buffer solution containing 6×SSC (1×SSC: 0.1~0.2 M NaCl, 0.01~0.02 M Sodium citrate, pH 6.5~7.5); 0.3~0.7% SDS; 5×Denhardt's solution (0.05~0.15% bovine serum albumin (BSA), 0.05~0.15% polyvinylpyrrolidone, 0.05~0.15% Ficoll 400); and 80~120 µg/ml salmon sperm DNA for 12~36 hours.

In particular, the oligonucleotide probe is not restricted in length. As a reference, it is composed of 15 nucleotides and preferably more than 18 nucleotides to prevent any non-specific hybridization.

The primer has no restriction as regards the nucleotide sequence and can include any DNA, if it can be annealed to the above DNA or DNA with complementary nucleotide sequences, and be elongated using DNA polymerase under the conventional conditions of a polymerase chain reaction.

In addition, although the length of the primers is not specifically limited, it is preferable to have 15 through 40 nucleotides and even more preferable to contain 17 through 30 nucleotides. The primers can be utilized to amplify the gene of the species in which the PCR method is initially performed.

The hybridization is accomplished by the procedure demonstrated in the manual of Molecular Cloning: A Laboratory Manual (T. Maniatis, et al., Second Edition, Cold Spring Harbor Laboratory, 1989).

To construct the high-expression vector in the present invention, the high-expression vector pHCE19T(II), commercially available from the Bioleaders corporation, is utilized to insert the DNA of glutamic acid racemase and construct the constitutively high-expression vector independent of antibiotics. The expression vector of the present invention can be stably expressed in a mutant strain auxotropic to D-glutamic acid as the host.

Figure 1:
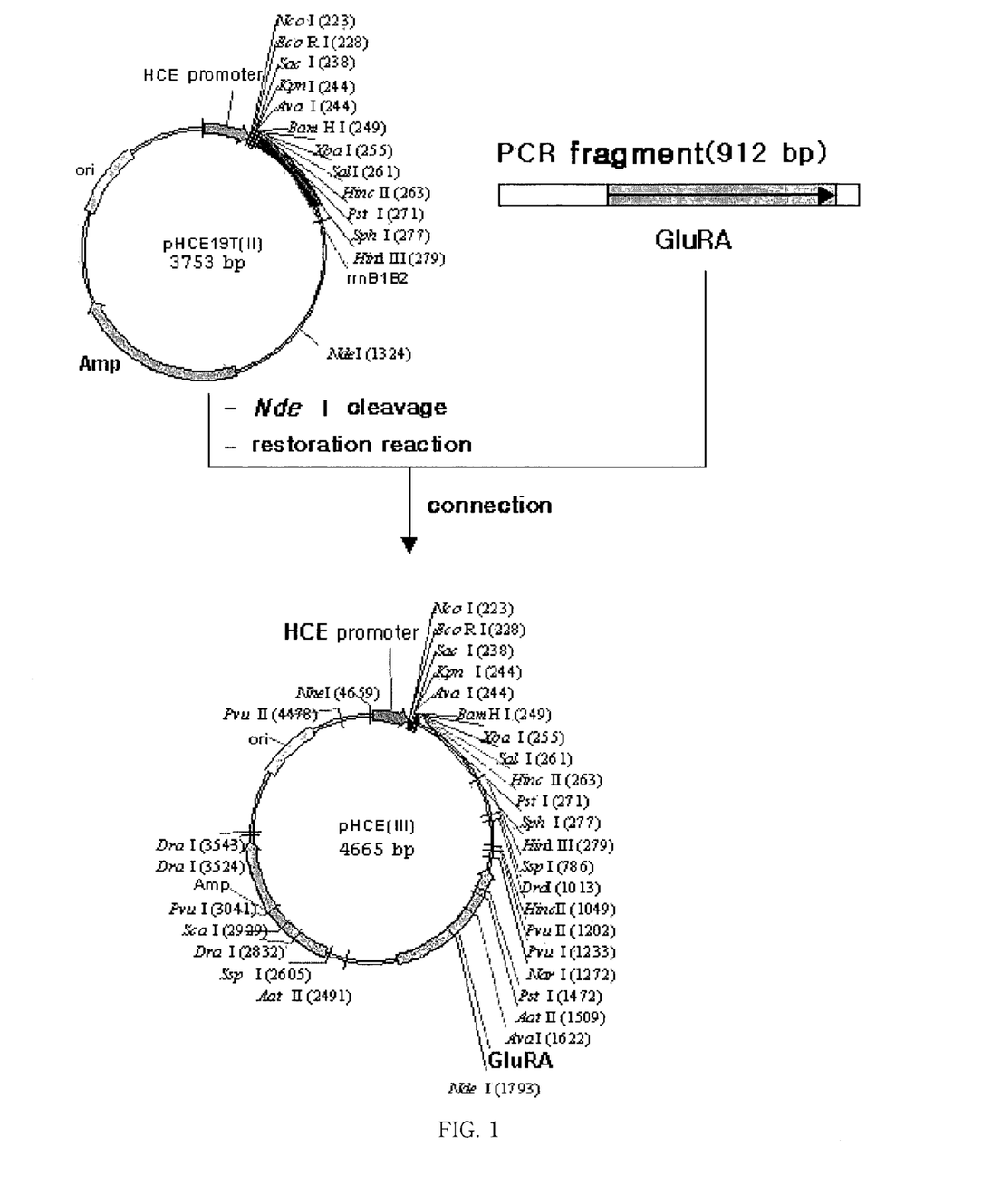
FIG. 1 is a schematic diagram of the procedure involved in the construction of the expression vector pHCE(III).

Concretely, the expression vector exploits the conventional and commercially available plasmid vector pHCE19T (II), as depicted in FIG. 1, which is cleaved using the Nde I restriction enzyme and filled with a Klenow fragment. Then, the cloned DNA of glutamic acid racemase is utilized as the template and amplified using synthetic oligonucleotides as primers, designed through general methods and made chemically, and PCR protocols. The resulting DNA fragment is introduced to the recognition site of the restriction enzyme Nde I in the expression vector pHCE19T(II) so as to construct the expression vector pHCE(III).

The expression vector pHCE19T(II) adopted in the present invention is composed of a constitutive promoter that can express a gene on a high level without an expensive inducer, such as IPTG, thereby being particularly suitable for exogenous gene production.

The proteins produced from the expression vector comprise about 30 through 50% of the total amount of soluble proteins and are expressed constitutively.

The constitutively high-expression vector described above confers a higher efficiency than conventional antibiotic-independent vectors, although this is not the purpose of the present invention. Therefore, it will be appreciated if those skilled in the art may deduce within the scope of the present invention.

In addition, the production of glutamic acid racemase from the expression vector pHCE(III) is sufficient to provide D-glutamic acid for cell growth, plus the amount of the enzyme is not excessive, so the expression of other genes products is unaffected. Advantageously, cells transformed using the expression vector pHCE(III) can be directly cultured onto a complex medium, LB medium, and the like, without any other filtration procedures.

In contrast, conventional techniques have various difficulties in cultivating auxotropic mutant strains, requiring the removal of any ions or metallic substances in the culture medium and the addition of specific amino acids or other carbon organic substances. However, the expression vector pHCE(III) in the present invention has settled these problems.

*E. coli* transformed by the expression vector pHCE(III) in the present invention was named *Escherichia coli* XL1-blue/pHCE(III), deposited with the International Deposit Organization, Korean Collection of Type Cultures (KCTC) at the Korean Research Institute of Bioscience and Biotechnology (KRIBB) on Dec. 29, 2000, and assigned accession number: KCTC 0925 BP. The expression vector pHCE(III) can be obtained from the deposited *Escherichia coli* strain.

Any kind of exogenous gene can be introduced to the expression vector in the present invention. For example, nucleic acids encoding proteins, nucleic acid encoding antisense RNA, nucleic acid encoding a decoy, nucleic acid encoding ribozyme, and the like. In addition, any kind of microbe can provide the exogenous gene described above. For example, the exogenous gene can be derived from microbes such as bacteria, yeasts, *Bacillus* sp., *Actinomyces* sp., *Ascomycetes* sp., *Basidiomycetes* sp. and so on; plants; insects; animals and the like, and depending on the occasion, can also include artificially synthesized genes.

Concretely, interleukine 1 through interleukine 12 genes, interferone α, β, and χ genes, a tumor necrosis factor gene, colony stimulating factor gene, erythropoietin gene, transformation proliferating factor β gene, immune globulin gene, tissue plasminogen activator gene, urokinase gene, firefly luciferase gene and the like are included within the scope of the exogenous gene, which does not limit the present invention.

In the specification of the present invention, "decoy" designates a nucleic acid encoding a transcription factor binding protein derived from a cell or DNA containing the sequence of the transcription binding site or similar sequences. When introduced to cells, a decoy has the functional activity of inhibiting the transcription factor. In addition, in the specification of the present invention, "ribozyme" is the cleaving mRNA of a specific protein and depicts an enzyme inhibiting the translation of specific proteins. Precisely, regardless of the kind of enzyme, for example, a hammer head type ribozyme, hairpin type ribozyme, delta type ribozyme, and the like, any enzyme can correspond to the ribozyme of the present invention if it can cleave the mRNA of specific proteins and inhibit the translation of the proteins.

Furthermore, in the present invention, the recombinant DNA and expression vector are utilized to obtain a transformed cell containing either the recombinant DNA or expression vector. In addition, the present invention provides a process for the preparation of useful proteins, in which transformed cells containing the recombinant DNA and expression vector are cultivated and the exogenous proteins are separated from the extract of the cultured cells. The processes related to the above preparation process are also within the scope of the present invention.

Precisely, the transformed cell is obtained by a transformation procedure using the expression vector containing the above recombinant DNA. The obtained transformed cell is cultivated and the cell extract separated to obtain the purified exogenous proteins.

As a reference, the protocols illustrated in Virology (Vol. 52, 456, 1973) and Journal of the National Cancer Institute (Vol. 41, 451, 1968) are applied to introduce the recombinant DNA to the host cells.

In addition, to transfer the expression vector into the host cells, the calcium phosphate method (Molecular and Cellular Biology, Vol. 7, 2745); electroporation method (Proceedings of the National Academy of Sciences USA, Vol. 81, 7161, 1984); DEAE-dextran method (Methods in Nucleic Acids Research, 283, CRC Press, 1991); and riposome method (BioTechiniques, Vol. 6, 682, 1989) etc. are referred.

BRIEF DESCRIPTION OF DRAWINGS

The above, along with other objectives, features, and advantages of the present invention will be more clearly understood from the following detailed description taken in conjunction with the accompanying drawings, in which.

DESCRIPTION OF THE EMBODIMENTS

The practical and presently preferred embodiments of the present invention are described in more detail below.

However, it is appreciated that those skilled in the art, on consideration of this disclosure, may make modifications and improvements within the scope of the present invention.

<Preferred Embodiment 1> Separation of Glutamic Acid Racemase from *Brevibacillus borstelensis*

To separate the DNA of glutamic acid racemase from *Brevibacillus* sp., the *Brevibacillus borstelensis* strain was inoculated to LB medium, cultured with shaking, and centrifuged. Then, the collected cells were recovered, made into protoplasts by treating with lysozyme, and lysed completely with the addition of sodium dodecyl sulfate (SDS). Thereafter, salts were added to the whole reaction solution and the proteins precipitated. Next, the reacted solution was centrifuged, only the supernatant was adopted from the separated protein, and phenol was added at the same volume as the supernatant to eliminate any contaminants, such as protein and the like, in the liquid phase. The above procedure was repeated several times. A double volume of ethanol was added to the phenol mixing solution (phenol:chloroform=1:1 in a volume ratio) and precipitated to remove any contaminants. The precipitated pellet was separated by being wired around a glass rod and washed with adding ethanol in a 70% concentration. The above pellet was then dissolved in a Tris-EDTA (TE) buffer solution containing ribonuclease to obtain DNA in which the RNA had been removed.

The above DNA was re-utilized as the template, and a gene with a size of 910 bp was cloned using the PCR method (See SEQ ID NO: 1).

The DNA of glutamic acid racemase was amplified through the PCR procedure using a promoter of glutamic acid racemase derived from *Brevibacillus borstelensis*, primer 1 upstream of the gene encoding the ORF, and primer 2 downstream of the gene.

Primer 1: 5'agc gaa aat aaa agg aag tg-3' (20 mer)

Primer 2: 5'gcg ttt att tgc cga ctc ag-3' (20 mer)

<Reaction Solution for PCR>

Primers 1 and 2 (concentration 10 mM): 1 µl respectively dNTP mixture (dATP, dTTP, dCTP, dGTP; 10 mM, respectively 2.5 mM): 4 µl 10×PCR buffer solution: 5 µl Ex Taq DNA polymerase (purchased from Takara Inc.): 0.2 µl DNA used as the template: 2 µl (200 ng)

Final volume: 50 µl

To perform the PCR, the experimental conditions were according to the Hot start method; precisely, reacted at 95° C. for 5 minutes, denatured at 95° C. for 30 seconds, primer-annealed at 55° C. for 1 minute, and polymerized at 72° C. for 2 minutes. If the above procedure is considered as 1 cycle, then 30 cycles were performed repeatedly and finally completed at 72° C. for 10 minutes.

DNA fragments containing the amplified glutamic acid racemase gene were treated with Klenow fragments (purchased from Borhrienger Mannheim) and purified in a blunt end state.

<Preferred Embodiment 2> Construction of Antibiotic-independent Vector pHCE(III) for Constant High-expression and Production of Transformed Cells (1) Construction of Antibiotic-independent Vector for Constant High-expression The expression vector pHCE19T(II) was cleaved with the Nde I restriction enzyme (1× buffer solution, 2 units of Nde I enzyme, DNA 2 µg), filled with a Klenow fragment, and purified using a BIO101 Gene Clean kit in spin mode. The above expression vector pHCE19T(II) fragment and glutamic acid racemase fragment were mixed in an approximate ratio of 1:3 mole concentration. Then, the reaction buffer solution for the DNA ligation (purchased from Takara Inc., DNA ligation kit Ver. 2) was mixed completely with the same volume and quantity of DNA and ligated at 16° C. for 12 hours. Thereafter, the expression vector pHCE(III) was obtained (See SEQ ID NO: 2).

To construct the expression vector pHCE(III) as a stable plasmid in a mutant strain auxotropic D-glutamic acid, a commercially available enzyme and kit were used for the gel purification (purchased from BIO101 Inc.) and plasmid purification (purchased from Roche Molecular Biochemicals Inc.).

FIG. 1 is a schematic diagram of the procedure involved in constructing the gene expression vector pHCE(III).

(2) Production of Transformed Cells

The completely dried DNA was re-dissolved in a Tris-EDTA (TE) buffer solution and transformed into a D-glutamic acid dependent auxotrophic mutant (*Escherichia coil* WM335 strain) through electroporation using a Gene-Pulser (purchased from Bio-Rad Inc.). The *E. coli* was cultured in 100 ml of LB medium until the OD value reached 0.6, and then separated by centrifuging at 6,000 rpm for 10 minutes. Next, the *E. coil* pellet was washed three times by adding 100 ml of 10% glycerol (aqueous solution) and a suspension prepared by the addition of 0.2 ml of 10% glycerol. 1 µg of the plasmid was added to 5 µl of the above suspension, stirred completely, and left in a 0.2 cm cuvette under ice for 10 minutes. Then, an electric current was applied to the cuvette while maintaining the following conditions: capacitance of 25 µF, 200 ohm, 2.5 kV, and duration period of 3 ms. One ml of LB medium was added to the above suspension, cultured at 37° C. for 1 hour, and smeared on an agar medium plate. The plasmid DNA was purified on a large scale from the transformed colonies that could grow in the complex medium without D-glutamic acid using a Plasmid Purification Kit (Jetstar 2.0 plasmid Midi Purification Kit; purchased from Genomed Inc.).

<Preferred Embodiment 3> Examination of Cellular Stability in Antibiotic-independent Vector for Constant High-expression To confirm the stability of the expression vector pHCE (III) in a medium without any antibiotics, the Tyrosine phenol lyase (TPL) gene, an industrially usable enzyme, was introduced to the expression vector.

(1) Construction of Expression Vector pHCE(III) Including Inserted TPL Gene

Figure 2:
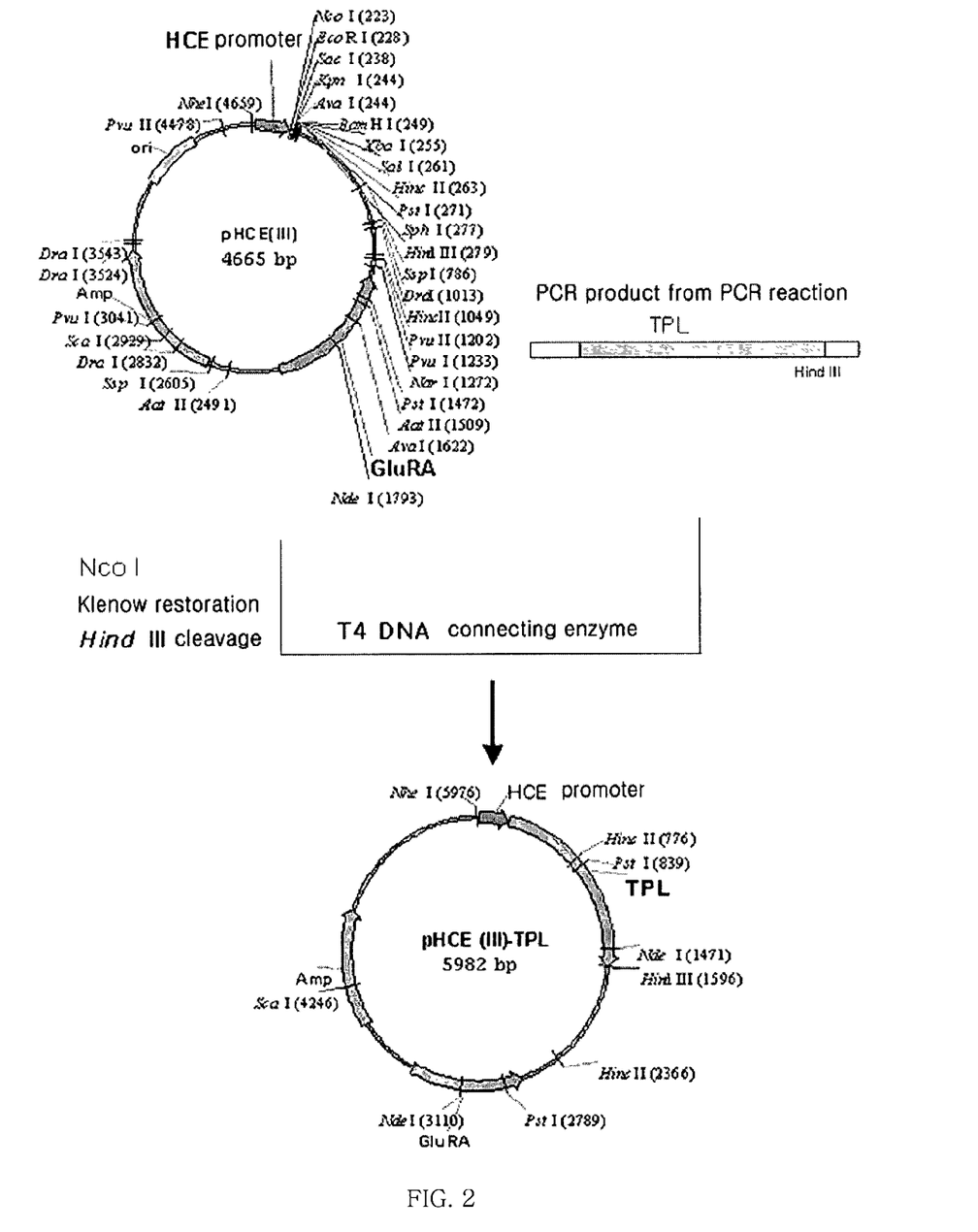
FIG. 2 is a schematic diagram of the procedure involved in the construction of the expression vector pHCE(III)-TPL for the stability test.

As illustrated in FIG. 2, the expression vector pHCE(III)-TPL was made. Concretely, the TPL gene was first amplified through the PCR method in which a plasmid vector pTPL containing the TPL gene was used as the template. At this point, the adopted primers were as follows.

Primer 1: 5'aat tat ccg gca gaa ccc ttc-3' (21 mer)

Primer 2: 5'cgg atc caa gct tat tag ata tag tca
          aag cgt gca gt-3' (38 mer)

The amplified TPL gene was purified by cleavage with the restriction enzyme Hind III. The expression vector pHCE (III) was treated with the restriction enzyme Nco I, the terminus restored with a Klenow fragment, and then cleaved again with the restriction enzyme Hind III. A fragment with a large molecular weight from among the fragments of the expression vector pHCE(III) treated with the restriction enzyme Hind III was then ligated with the TPL gene obtained above, thereby producing the expression vector pHCE(III)-TPL.

(2) Production of Transformed Cells

The transformed cells were prepared under the same conditions using the electroporation method described in preferred embodiment 2. The expression vector pHCE(III)-TPL was introduced into the host, *E. coli* WM335[leu pro trp his arg thyA deoB met lac gal xyl ara mal lam phx rpsL hsdS-K12 glt], a D-glutamic acid dependent auxotropic strain, so as to obtain the transformed cells.

The transformed cells were cultured in LB medium containing 10 g/L of tryptone (purchased from Difco Inc.), 5 g/L of yeast extract (purchased from Difco Inc.) and 10 g/L of NaCl.

(3) Examination of Highly Expressed TPL

To identify the stability of the expression vector pHCE (III) and expression of the targeted TPL, culture conditions without antibiotics were utilized.

The transformed cells obtained above were cultivated through 9 generations and separated by centrifuging the transformed cells of each of the 9 generations at 5000×g for 20 minutes. The plasmid stability of the cells was confirmed using a plasmid purification kit (High pure plasmid isolation kit: purchased from Roche Inc.)

Figure 3A:
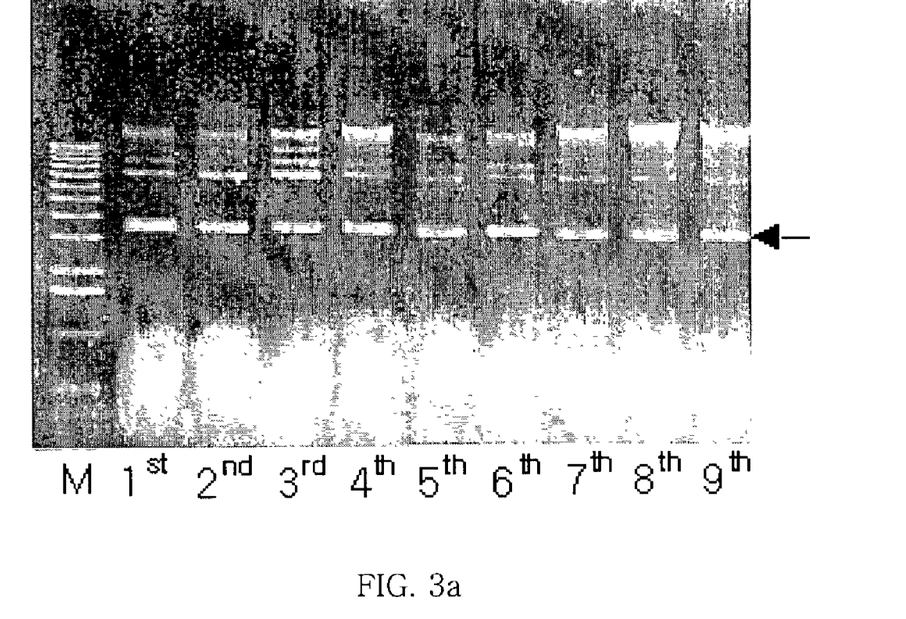
FIG. 3a depicts a stability analysis of the expression vector pHCE(III)-TPL based on agarose gel electrophoresis.

As depicted in FIG. 3a, the stability of the plasmid was maintained through 9 successive generations.

In addition, the transformed cells separated by centrifuging the cells from the same period at 5000×g for 20 minutes were washed with a 1X Phosphate Buffer Saline (PBS) buffer (pH 7.6). The collected cells were suspended in a buffer solution of 0.1M Tris-Cl (pH 8.0). The obtained cells were then sonicated using an ultrasonicator (purchased from Branson Ultrasonics Inc.) and centrifuged at 20000×g for 20 minutes to eliminate any cell debris and obtain a supernatant.

Figure 3B:
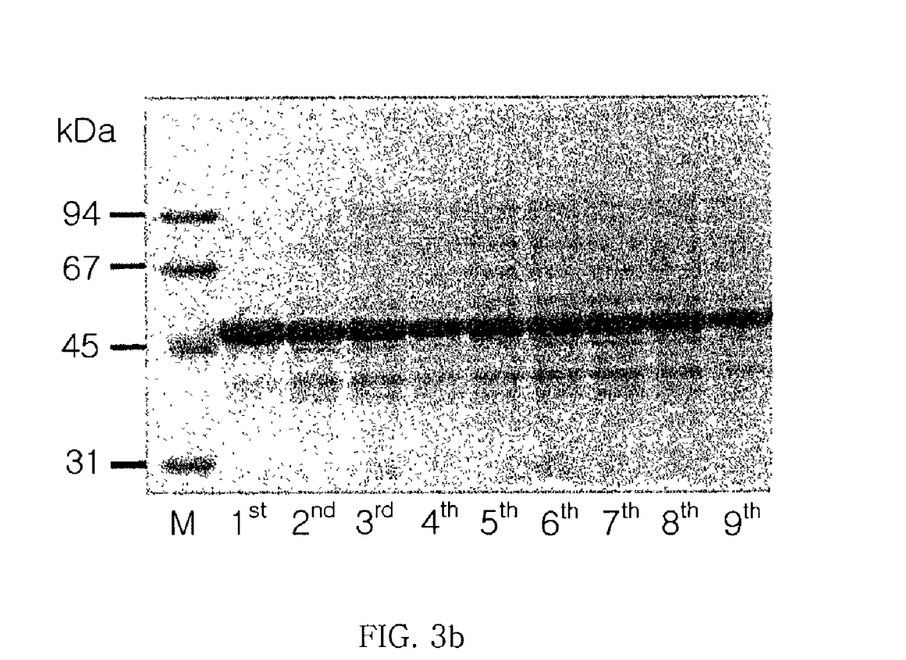
FIG. 3b presents an analysis of the high expression of the exogenous protein TPL through 9 generations based on SDS-polyacrylamide gel electrophoresis.

To confirm the high-expression of TPL, the supernatant was analyzed by performing electrophoresis through SDS-PAGE. As a result, even without the addition of an inducer, the production of TPL was found to represent more than about 40% of the soluble proteins within a whole cell, as represented in FIG. 3b.

<Preferred Embodiment 4> Expression of TNA Enzyme Using Antibiotic-independent Vector for Constant High-expression As certified in preferred embodiment 3, the expression vector pHCE(III) obtained in the present invention was confirmed to be stable. To analyze the possibility of manufacturing purposed proteins using the above stable vector, an experiment for manufacturing TNA in the mutant strain auxotropic D-glutamic acid WM335 was performed based on cloning the tryptophan indol lyase (TNA) gene derived from thermophilic Bacillus, Symbiobacterium toebii SC-1 utilizing the expression vector pHCE(III).

(1) Construction of Expression Vector Containing TNA Gene

Figure 4:
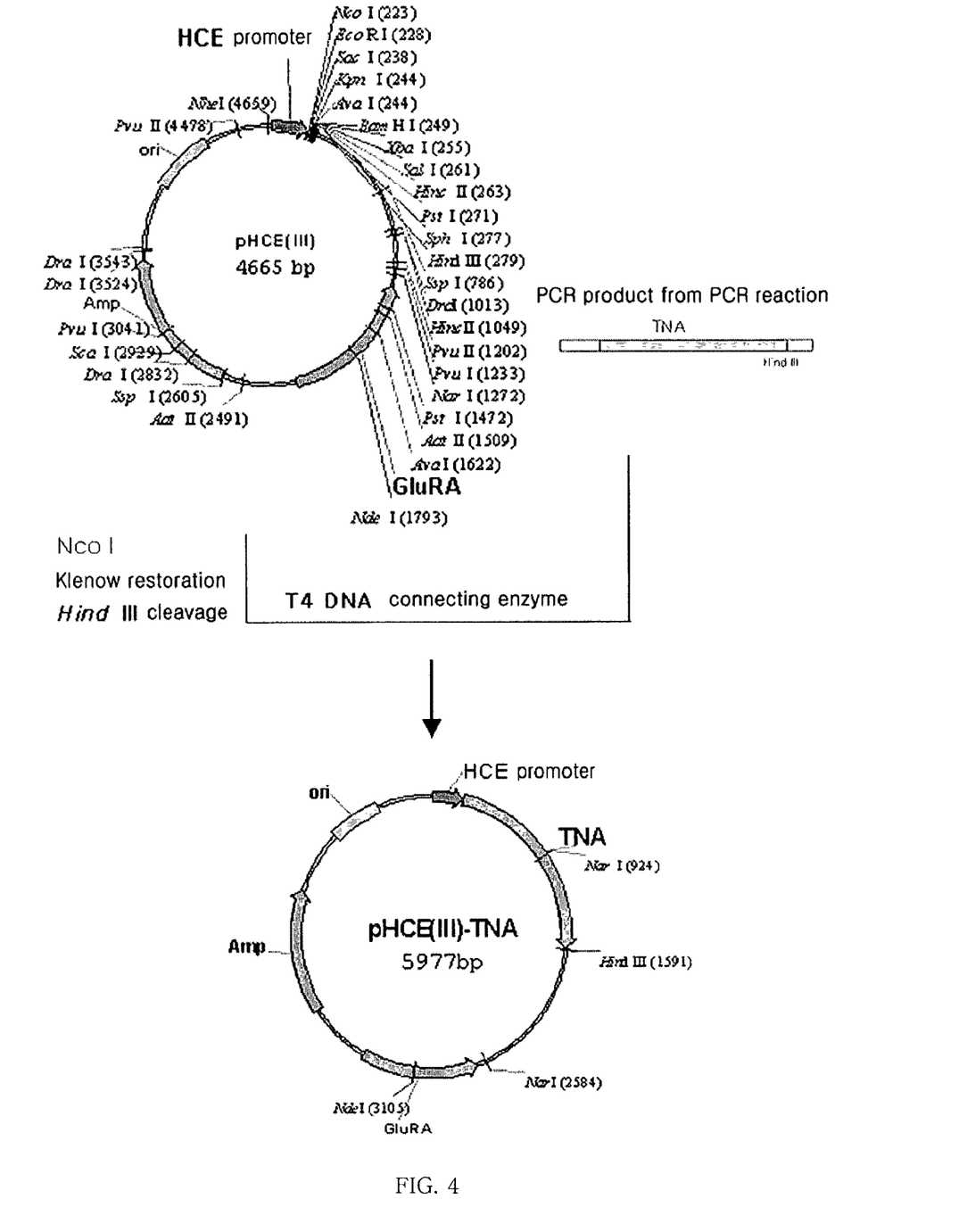
FIG. 4 is a schematic diagram of the procedure involved in constructing the expression vector pHCE(III)-TNA containing the TNA gene.

As demonstrated in FIG. 4, pHCE(III)-TNA was made using the expression vector pHCE(III).

The TNA gene was amplified through the PCR method in which a plasmid vector pTNA containing the TNA gene was used as the template. The adopted primers were as follows.

```
Primer 1: 5'cca aag ggc gag ccc ttt aa-3' (20 mer)

Primer 2: 5'tga cta agt ctg cag aag ctt att aga cca
          gat cga agt ggc-3' (42 mer)
```

The amplified TNA gene was purified by cleavage with the restriction enzyme Hind III. Then the expression vector pHCE(III) was treated with the restriction enzyme Nco I, the terminus restored using a Klenow fragment, and then cleaved again with the restriction enzyme Hind III. A fragment with a large molecular weight selected from among the fragments of the expression vector pHCE(III) treated with the restriction enzyme Hind Ill was then ligated with the TNA gene obtained above, thereby producing pHCE(III)-TNA.

(2) Production of Transformed Cells

Transformed cells were prepared using the electroporation method described in preferred embodiment 2. The expression vector pHCE(III)-TNA was introduced into a host, E. coli WM335[leu pro trp his arg thyA deoB met lac gal xyl ara mal lam phx rpsL hsdS-K12 glt], a D-glutamic acid dependent auxotropic strain, to obtain the transformed cells.

The transformed cells were then was cultured in LB medium containing 10 g/L of tryptone (purchased from Difco Inc.), 5 g/L of yeast extract (purchased from Difco Inc.) and 10 g/L of NaCl.

(3) Examination of Plasmid Stability

Figure 5A:
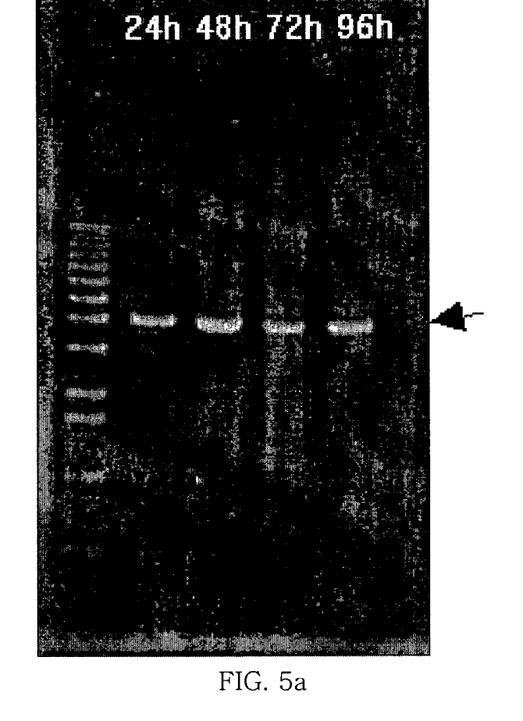
FIG. 5a presents a stability analysis of the expression vector pHCE(III)-TNA based on agarose gel electrophoresis.

The transformed cells described above (2) were cultivated through 3 generations in a 100 ml-flask without the addition of any antibiotics, then the transformed cells of each of the 3 generations were separated by centrifuging at 5000×g for 20 minutes. The plasmid stability was certified using a plasmid purification kit(High pure plasmid isolation kit: purchased from Roche Inc.). As demonstrated in FIG. 5a, the plasmid was confirmed to continually and stably exist in the cells.

(4) Examination of Highly Expressed TNA

Figure 5B:
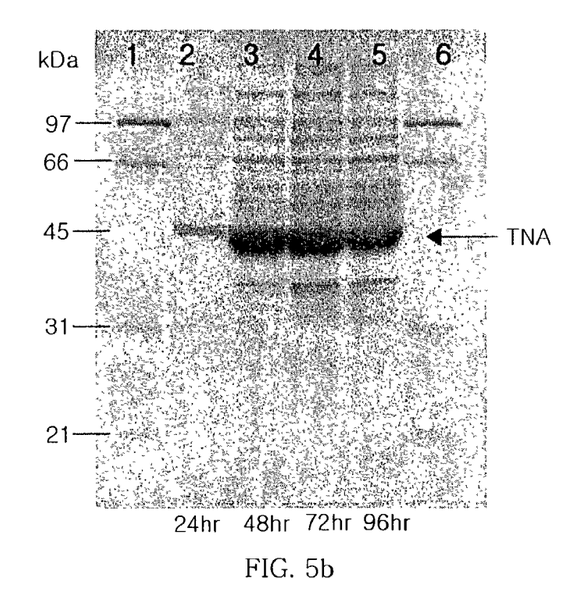
FIG. 5b presents an analysis of the high expression of the exogenous protein TNA based on SDS-polyacrylamide gel electrophoresis.

The transformed cells separated by centrifuging at 5000×g for 20 minutes, as described above, were washed with a 1× Phosphate Buffer Saline (PBS) buffer (pH 7.6). The collected cells were then suspended in a buffer solution of 0.1 M Tris-Cl (pH 8.0). The suspended cells were sonicated using an ultrasonicator (purchased from Branson Ultrasonics Inc.) and then centrifuged at 20000×g for 20 minutes to eliminate any cell debris and obtain the supernatant. To confirm a high-expression of TNA, the supernatant was analyzed by performing electrophoresis through SDS-PAGE. As a result, the continual and high expression of TNA was confirmed, as depicted in FIG. 5b.

(5) Mass Production of TNA

TNA was manufactured by culturing E. coli WM335/pHCE(III)-TNA containing the expression vector pHCE(III)-TNA. As a result, the TNA produced represented about 40% of the proteins in the E. coli. The E. coli (WM335/pHCE(III)-TNA) was cultured in a complex medium containing 50 g/l of glycerol to manufacture TNA based on a high cell growth in a batch culture.

Figure 6:
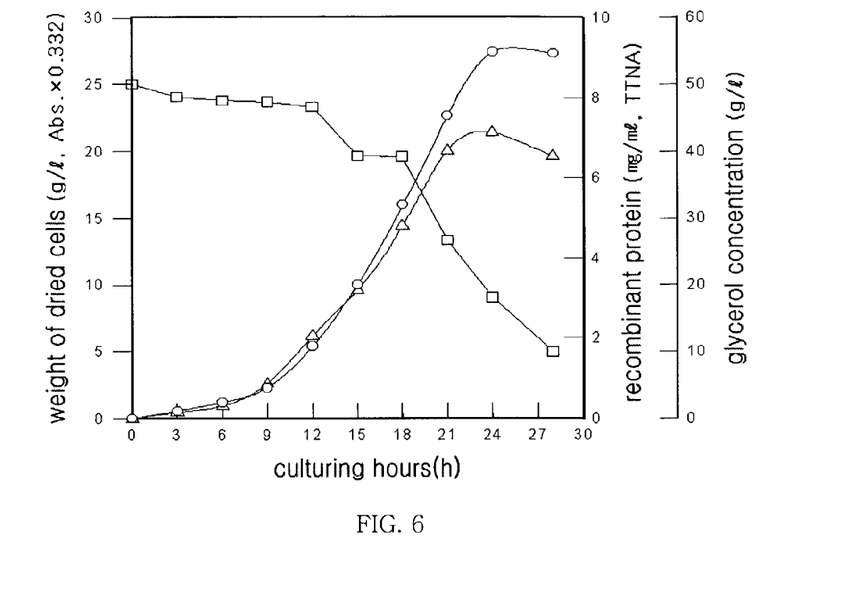
FIG. 6 depicts the mass production of the biocatalyst TNA when using recombinant *Escherichia coli* WM335/pHCE(III)-TNA.
Figure 7:
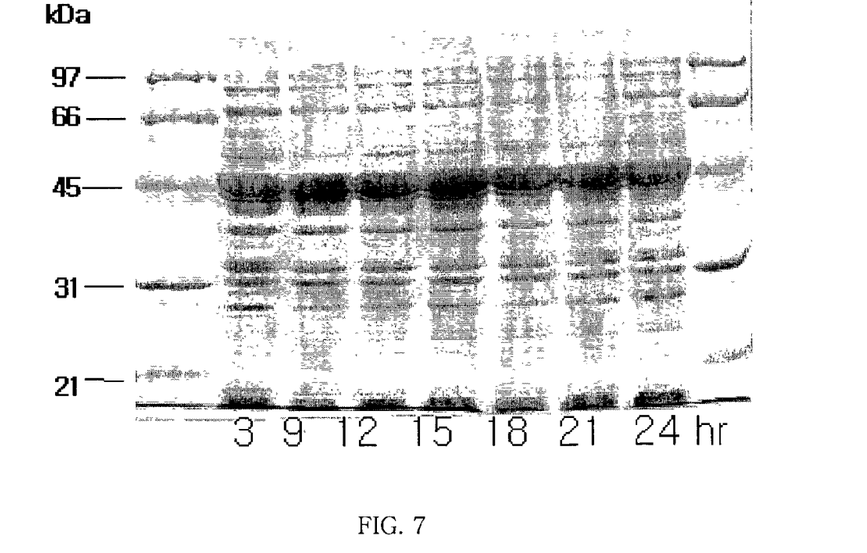
FIG. 7 shows the use of SDS Polymeric gel electrophoresis to identify the mass production of the biocatalyst TNA when using recombinant *Escherichia coli* WM335/pHCE(III)-TNA.

A growth curve representing the batch culture of the E. coli (WM335/pHCE(III)-TNA) that grew in a 2.5 L fermentor at 37° C. and 700 rpm is illustrated in FIG. 6. In FIG. 6, the mark—○— indicates the dried cell weight (g/l), the mark—△— represents the synthetic activity of TNA (unit/ml), and the mark—□— indicates the concentration of glycerol (g/l). After culturing for 3 hours, the production of TNA increased in accordance with the cell growth and maintained a high-expression level throughout the growth period. The final cell concentration exhibited a 75 degree optical density at 600 nm and the maximum activity of TNA reached 3,450 unit/ml after culturing for 24 hours.

The protein band that appeared through SDS-PAGE was analyzed using a scanning densitometer and, as a result, the TNA content in the soluble enzyme was estimated to represent about 40% of the protein in a whole cell acquired from the extracts of the E. coli.

The result that the expression vector was able to maintain a stable and high expression without the addition of antibiotics suggests the feasibility of applying this effective high-expression system to the production of other recombinant proteins.

INDUSTRIAL APPLICABILITY

As demonstrated and confirmed above, the present invention relates to a high-expression vector in which a recombinant gene can be stably transcribed and highly expressed using genes essential for cell growth and proliferation as a selective marker without the need for any antibiotic-resistant genes, such as ampicillin and the like.

The antibiotic-independent high-expression vector in the present invention resolves the problems related to expensive inducers and the use of genes resistant to antibiotics. Accordingly, the expression vector in the present invention can be widely applied for the high expression of various kinds of useful DNA and production of exogenous proteins on a large scale, with no adverse affect on the environment.

What is claimed:

1. An isolated nucleic acid sequence consisting of the full-length nucleotide sequence disclosed in SEQ ID NO:1 or nucleotides 64–893 of SEQ ID NO:1.

2. A plasmid vector comprising the nucleic acid sequence of claim 1.

3. The plasmid vector of claim 2 further comprising an exogenous gene.

4. The plasmid vector of claim 3 wherein the plasmid vector comprises a phage vector or a viral vector.

5. The plasmid vector of claim 2 wherein the plasmid vector consists of the nucleotide sequence disclosed in SEQ ID NO:2.

6. An isolated bacterial cell comprising the plasmid vector of claim 3.

7. A method of producing a protein comprising:
   a) transforming an *E. coli* WM335 cell with the plasmid vector of claim 3,
   b) culturing the transformed cell in the absence of any antibiotic such that a protein encoded by said exogenous gene is expressed, and
   c) recovering the expressed protein from the cultured cell or from the culture supernatant.

* * * * *